United States Patent [19]

Maisey

[11] 4,033,951

[45] July 5, 1977

[54] MORPHOLINE DERIVATIVE OF A 1,4-BENZOTHIAZIN-3-ONE

[75] Inventor: Roy Frederick Maisey, Macclesfield, England

[73] Assignee: Imperial Chemical Industries Limited, London, England

[22] Filed: June 22, 1976

[21] Appl. No.: 698,780

Related U.S. Application Data

[62] Division of Ser. No. 528,578, Nov. 29, 1974, Pat. No. 3,989,699.

[30] Foreign Application Priority Data

Dec. 13, 1973 United Kingdom ............ 57743/73

[52] U.S. Cl. .................. 260/243 R; 424/246; 260/247.2 A
[51] Int. Cl.² .......................... C07D 279/16
[58] Field of Search ................ 260/243 R

[56] References Cited

UNITED STATES PATENTS

| | | |
|---|---|---|
| 3,714,161 | 1/1973 | Malllon .................. 260/247.7 C |
| 3,725,403 | 4/1973 | Krapcho ......................... 260/243 |
| 3,733,321 | 5/1973 | Krapcho ......................... 260/243 |
| 3,767,653 | 10/1973 | Krapcho ......................... 260/243 |

FOREIGN PATENTS OR APPLICATIONS 1,224,815   2/1960   France

Primary Examiner—John M. Ford
Attorney, Agent, or Firm—Cushman, Darby & Cushman

[57] ABSTRACT

The disclosure relates to new morpholine derivatives which possess antidepressant activity, to processes for the manufacture of said derivatives and to pharmaceutical compositions containing them. Typical of the morpholine derivatives disclosed is 2-(4H-2,3-dihydro-1,4-benzoxazin-3-one-4-ylmethyl)morpholine.

3 Claims, No Drawings

MORPHOLINE DERIVATIVE OF A 1,4-BENZOTHIAZIN-3-ONE

This is a division of application Ser. No. 528,578 filed Nov. 29, 1974 now U.S. Pat. No. 3,989,699.

This invention relates to morpholine derivatives which possess antidepressant properties.

According to the invention there is provided a morpholine derivative of the formula:

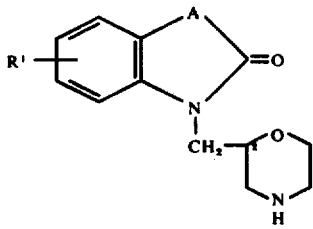

wherein $R^1$ stands for a hydrogen or halogen atom or an alkyl or alkoxy radical of 1 to 3 carbon atoms and A stands for an oxygen atom or a methylene radical, or for a radical of the formula:

wherein $R^2$ and $R^3$, which may be the same or different, stand for hydrogen atoms or for alkyl radicals of 1 to 3 carbons atoms and B stands for an oxygen or sulphur atom or a methylene radical or alkylmethylene

radical in which the alkyl group is of 1 to 3 carbon atoms, and the pharmaceutically-acceptable acid-addition salts thereof.

It will be observed that the compound of the invention contains at least one asymmetric carbon atom, that marked 2 in formula I, and in addition when A stands for a radical of the formula:

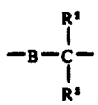

in which $R^2$ and $R^3$ are different, the carbon atom to which they are attached is also asymmetric. The racemic form of the compound of the formula I may therefore be resolved into 2 or 4 optically-active enantiomeric forms. It is to be understood that this invention encompasses the racemic form of the compound of the formula I, and each optically-active enantiomeric form.

A particular value for $R^1$ when it is a halogen atom is a chlorine or bromine atom.

Particular groups of compounds of the invention within the above definition are as follows:

Those wherein $R^1$ stands for a hydrogen or halogen atom or an alkyl or alkoxy radical of 1 to 3 carbon atoms and A stands for a radical of the formula:

wherein $R^2$ and $R^3$, which may be the same or different, stand for hydrogen atoms or for alkyl radicals of 1 to 3 carbon atoms and B stands for an oxygen or sulphur atom or a methylene radical:

Those wherein $R^1$ stands for a hydrogen or halogen atom or an alkyl or alkoxy radical of 1 to 3 carbon atoms and A stands for a radical of the formula:

wherein $R^2$ and $R^3$ stand for hydrogen atoms and B stands for an oxygen or sulphur atom or a methylene radical:

Those wherein $R^1$ stands for a hydrogen or chlorine atom or a methyl, methoxy or n-propoxy radical and A stands for an oxygen atom or a methylene radical, or for a radical of the formula:

wherein $R^2$ and $R^3$, which may be the same or different, stand for hydrogen atoms or methyl radicals and B stands for an oxygen or sulphur atom or a methylene radical or methylmethylene

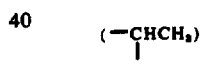

radical:

Those wherein $R^1$ stands for a hydrogen or halogen atom or for an alkyl or alkoxy radical of 1 to 3 carbon atoms and A stands for a radical of the formula:

wherein $R^2$ and $R^3$, which may be the same or different, stand for hydrogen atoms or for alkyl radicals of 1 to 3 carbon atoms and B stands for an oxygen atom or a methylene radical or alkylmethylene

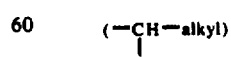

radical in which the alkyl group is of 1 to 3 carbon atoms:

Those wherein $R^1$ stands for a hydrogen or halogen atom or for an alkyl or alkoxy radical of 1 to 3 carbon atoms and A stands for a radical of the formula:

wherein R² and R³, which may be the same or different, stand for hydrogen atoms or for alkyl radicals of 1 to 3 carbon atoms and B stands for an oxygen atom or a methylene radical:

Those wherein R¹ stands for a hydrogen or halogen atom or for an alkyl or alkoxy radical of 1 to 3 carbon atoms and A stands for a radical of the formula:

wherein R² and R³, which may be the same or different, stand for hydrogen atoms or for alkyl radicals of 1 to 3 carbon atoms, and B stands for an oxygen atom:

Those wherein R¹ stands for a hydrogen or halogen atom or for an alkyl or alkoxy radical of 1 to 3 carbon atoms and A stands for a radical of the formula:

wherein R² and R³ stand for hydrogen atoms and B stands for an oxygen atom or methylene radical:

Those wherein R¹ stands for a hydrogen or halogen atom or for an alkyl or alkoxy radical of 1 to 3 carbon atoms and A stands for a radical of the formula:

wherein R² and R³ stand for hydrogen atoms and B stands for an oxygen atom:

Those wherein R¹ stands for a hydrogen or chlorine atom or a methyl, methoxy or n-propoxy radical and A stands for a radical of the formula:

wherein R² and R³, which may be the same or different, stand for hydrogen or methyl radicals and B stands for an oxygen atom or a methylene radical or methylmethylene

(—CHCH₃)

radical:

Those wherein R¹ stands for a hydrogen or chlorine atom or for a methoxy or methyl radical and A stands for a radical of the formula:

wherein R² and R³ stand for hydrogen atoms and B stands for an oxygen atom or a methylene radical:

Those wherein R¹ stands for a hydrogen or chlorine atom or for a methoxy or methyl radical and A stands for a radical of the formula:

wherein R² and R³ stand for hydrogen atoms and B stands for an oxygen atom.

Particular compounds of the invention are described in the Examples and of those preferred compounds are 2-(4H-2,3-dihydro-1,4-benzoxazin-3-one-4-ylmethyl)-morpholine and 2-(4H-2,3-dihydro-5-methyl-1,4-benzoxazin-3-one-4-ylmethyl)morpholine and the salts thereof as defined above.

A suitable pharmaceutically-acceptable acid-addition salt of the morpholine derivative of the invention is, for example, a hydrochloride, hydrobromide, phosphate or sulphate, or a citrate, acetate, maleate or oxalate.

The morpholine derivative of the invention may be manufactured by methods known in themselves for the manufacture of chemically analogous compounds, for example:

a. replacing by hydrogen the α-aryl-alkyl or alkyl radical in a compound of the formula:

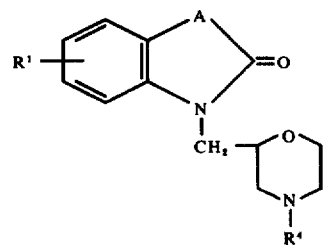

II wherein R¹ and A have the meanings stated above and R⁴ is an α-aryl-alkyl or alkyl radical. The α-aryl-alkyl radical may be such a radical of up to 11 carbon atoms, preferably the benzyl radical, and the alkyl radical may be such a radical of 1 to 6 carbon atoms, for example the isopropyl radical.

When A is a radical of the formula:

in which B is other than a sulphur atom, the α-aryl-alkyl radical may be replaced by hydrogen by hydrogenolysis. The hydrogenolysis is preferably carried out by means of hydrogen in the presence of a palladium-on-charcoal catalyst. The catalytic hydrogenolysis is conveniently carried out at ambient temperature and atmospheric pressure, and is conveniently accelerated by the presence of an acidic catalyst, for example hydrochloric acid.

Alternatively the α-aryl-alkyl or alkyl radical may be replaced by hydrogen by reaction with an aryl or alkyl chloroformate followed by replacement of the resulting aryl-or alkyl-oxycarbonyl group by hydrogen. The reaction with the aryl or alkyl chloroformate, for example phenyl, ethyl or 2,2,2-trichloroethyl chloroformate, may be carried out in a diluent or solvent, for example toluene or methylene chloride. When the alkyloxycarbonyl derivative is of at least 3 carbon atoms and is substituted on the β-carbon atom of the alkyl group by at least one chlorine or bromine atom, the alkoxy-carbonyl radical may be replaced by hydrogen by reaction with zinc, for example by zinc in the presence of a dilute acid, for example acetic acid. Alternatively, the aryl- or alkyl-oxycarbonyl derivative may be hydrolysed by reaction with an acid, for example hydrobromic or hydrochloric acid, in a diluent or solvent such as acetic acid, ethanol or water or a mixture of any two of these. All the above reactions may be accelerated or completed by the application of heat, for example by heating to the boiling point of the diluent or solvent.

b. for a compound of the formula I given above wherein A stands for an oxygen atom or for a radical of the formula:

wherein B stands for an oxygen or sulphur atom, reaction of a compound of the formula:

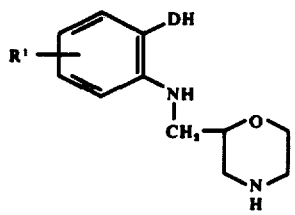

wherein $R^1$ has the meaning stated above and D is an oxygen or sulphur atom, with a carboxylic acid of the formula X—E—COOH or an activated derivative thereof, wherein X stands for a displaceable radical and E is either a direct bond or a radical of the formula:

wherein $R^2$ and $R^3$ have the meaning stated above. X may be, for example, a halogen atom, for example a chlorine or bromine atom, or a methanesulphonyloxy or toluene-p-sulphonyloxy radical. A suitable activated derivative of the carboxylic acid of the formula X—E—COOH is, for example, an ester, for example the ethyl ester, an acid halide, for example the acid chloride or bromide, or the anhydride or a mixed anhydride. When the reactant is the acid X—E—COOH or an ester thereof, the reaction is conducted under basic conditions. The compound of the formula III may, for example, be used in the form of a salt, for example a sodium salt, and the reaction may be conducted in a diluent or solvent, for example dimethyl formamide or ethanol. When the activated derivative of the acid X—E—COOH is an acid halide, the anhydride or a mixed anhydride, the reaction is conducted initially under acidic conditions, for example at a pH of below 4, and then under basic conditions, for example at a pH of above 10. The reaction may be conducted in a diluent or solvent, for example acetone or aqueous acetone.

c. for a compound of the formula I given above wherein A stands for a radical of the formula:

wherein B stands for an oxygen or sulphur atom and $R^3$ stands for a hydrogen atom, decarboxylation of a compound of the formula:

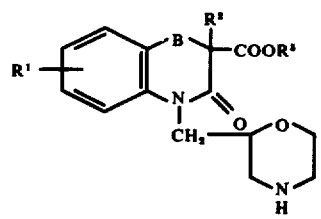

wherein $R^1$, $R^2$ and B have the meanings stated above and $R^5$ is a hydrogen atom or an alkyl radical. $R^5$ may, for example, be an alkyl radical of 1 to 6 carbon atoms, for example the ethyl radical. The decarboxylation may be carried out in a diluent or solvent, for example water or ethanol, and it may be carried out by heating, for example by heating to the boiling point of the diluent or solvent. The reaction may be carried out in the presence of an acid or a base, for example hydrochloric acid or sodium hydroxide.

d. cyclisation of a compound of the formula:

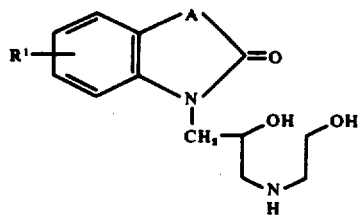

wherein $R^1$ and A have the meanings stated above. The reaction may be carried out in a diluent or solvent, for example xylene or water, in the presence of an acid, for example toluene-p-sulphonic or hydrobromic acid, and it may be accelerated or completed by the application of heat.

e. for a compound which is an optically-active enantiomer, resolution of the racemic compound of the formula I given above by conventional means, or by use of any of processes (a) to (d) above in which the intermediate of the formula II, III, IV or V is itself a resolved isomer.

The starting material of the formula II for use in process (a) may be prepared by reaction of the sodium salt of a compound of the formula:

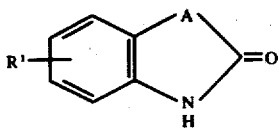

VI with a compound of the formula:

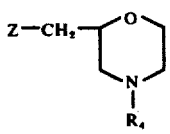

VII wherein Z is a chlorine or bromine atom or a toluene-p-sulphonyloxy radical.

The starting material of the formula III for use in process (b) may be prepared by reaction of a compound of the formula:

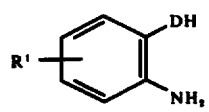

VIII with a compound of the formula VII above in which $R^4$ is the benzyl radical followed by replacement by hydrogen of the benzyl group in the product. This may be achieved by hydrogenolysis or by treatment with 2,2,2-trichloroethyl chloroformate followed by reaction of the resulting intermediate with zinc in a dilute acid.

The starting material of the formula IV for use in process (c) may be prepared by reaction of the sodium salt of the compound of the formula III used in process (b) with a compound of the formula:

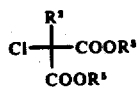

IX

The starting material of the formula V for use in process (d) may be prepared by reaction of the sodium salt of the compound of the formula VI above with epichlorhydrin followed by reaction of the epoxide thus formed with ethanolamine.

The compounds of the invention possess antidepressant activity in warm-blooded animals and this can be demonstrated by their ability to counteract the hypothermia normally induced by reserpine in mice. This effect is the one primarily used in the art for establishing the relative antidepressant activity in a series of chemically-related compounds. This counteraction can be demonstrated by the reversal of reserpine-induced hypothermia, a test known as the RHL test, which is described in Askew, Life Sciences, 1963, 2, 725. The counteraction can alternatively be demonstrated by the antagonism of reserpine hypothermia, a test known as the RHH test, which is described in Garattini et al., J. Pharm. Pharmacol., 1962, 14, 509. The RHL test is carried out as follows:

Mice are kept in a constant temperature room maintained at 21° ± 1° C. Each member of groups of 4 mice is given reserpine (2 mg. of base per kg. bodyweight, given subcutaneously as the acetate). Seventeen hours later the oesophageal temperature ($T_O$) of each mouse is recorded by means of an orally-inserted probe coupled to an electric thermometer which is calibrated in degrees Centigrade and which can be read to 0.1° C. Immediately after the temperature measurement the mice are dosed orally with the test compound, or with imipramine, each mouse in a group of four being given the same substance, and the oesophageal temperatures are again recorded after 4 hours ($T_4$). The compound under test is dosed at serial dilutions, e.g. 100, 30, 10, 3, 1, 0.3, 0.1 mg./kg. Imipramine is used as the control. Over a large number of tests it has been found that 3 mg./kg. of imipramine produces an average rise in the temperature of a reserpinised mouse of 3° C. At 1 mg./kg. it produces an average rise of 1.7° C. A test compound which at a certain dose level gives a rise in temperature equal to or greater than that given by 1 mg./kg. of imipramine, dosed to a different set of mice on the same day, is adjudged "active" at that dose. The RHH test is carried out as follows:

Mice are kept in a constant temperature room maintained at 21° ±1° C. The oesophageal temperature of each mouse in a groupd of six is recorded by means of an orally-inserted probe coupled to an electric thermometer which is calibrated in degrees Centigrade and which can be read to ± 0.1° C. Immediately after the temperature measurement the mice are dosed orally with the test compound or with saline (controls). One hour later the temperatures are again taken ($T_O$) and the mice are treated with reserpine (2 mg. of base per kg. bodyweight, given intravenously as the acetate). Temperatures are subsequently recorded at 1, 2 and 4 hours after reserpine injection ($T_1$, $T_2$ and $T_4$ respectively). The effect of the test compound is computed from the mean cumulative decrease in temperature, $T_D$, compared to that of the controls given reserpine alone, $T_R$, calculated according to the following equation:

$$T_D \text{ or } R = 3T_O - (T_1 + T_2 + T_4)$$

The $ED_6$ is that dose level of drug which produces a cumulative temperature decrease ($T_D$) of 6° C. less than that of controls ($T_R$). All the compounds exemplified in this specification are active on the RHL test, or have an $ED_6$ on the RHH test, at less than or equal to 100 mg./kg. of free base.

The compound of the invention 2-(4H-2,3-dihydro-1,4-benzoxazin-3-one-4-ylmethyl)morpholine hydrogen oxalate has an $LD_{50}$ in mice of 800 mg./kg. when dosed orally.

According to a further feature of the invention there is provided a pharmaceutical composition which comprises as active ingredient a morpholine derivative of the invention in association with a non-toxic pharmaceutically-acceptable diluent or carrier.

The pharmaceutical composition may be, for example, in a form suitable for oral or parenteral administration, for which purposes it may be formulated by means known to the art into the form of, for example, tablets, capsules, aqueous or oily solutions or suspensions, emulsions, sterile injectable aqueous or oily solutions or suspensions, or dispersible powders.

The pharmaceutical composition of the invention may also contain, in addition to the morpholine derivative or salt thereof, one or more known drugs selected from neuroleptic-sedative agents, for example chlorpromazine, prochlorperazine, trifluoperazine and haloperidol; other sedative drugs and tranquillizers, for example chlordiazepoxide, phenobarbitone and amylobarbitone; β-adrenergic blocking agents, for example propranolol; drugs used in the treatment of Parkinson's disease, for example benzhexol; and other antidepressant drugs, for example imipramine, desipramine, amitripyline, and nortriptyline; drugs of the amphetamine type; and monoamineoxidase inhibitors, for example phenelzine and mebanazine.

A preferred pharmaceutical composition of the invention is one suitable for oral administration in unit dosage form, for example tablets and capsules, which contain between 20 and 200 mg. of active ingredient, or one suitable for intravenous or intramuscular injection, for example a sterile aqueous solution containing between 0.5 and 4% w/w of active ingredient.

The pharmaceutical composition of the invention will normally be administered to man for the treatment or prophylaxis of depressive illness at such a dose that each patient receives a total oral dose of between 50 mg. and 1 g. of active ingredient per day, or a total intravenous or intramuscular dose of between 10 and 200 mg. per day, the composition being administered 2 or 3 times per day.

The invention is illustrated, but not limited, by the following Examples:

EXAMPLE 1

A solution of 4-benzyl-2-(4H-2,3-dihydro-1,4-benzoxazin-3-one-4-ylmethyl)morpholine hydrogen oxalate (10.4 g.) in ethanol (50 ml.) and water (100 ml.) was hydrogenated over 5% palladium-on-charcoal (1 g.) at room temperature and atmospheric pressure until a molar equivalent of hydrogen had been absorbed. Filtration of the mixture and evaporation of the solvents in vacuo afforded a residue which was triturated with ethanol, then added to a 50% aqueous solution of sodium hydroxide (20 ml.). Extraction of the mixture with ethyl acetate yielded an oil which was converted to a maleate salt by standard procedures then crystallised from methanol to give 2-(4H-2,3dihydro-1,4-benzoxazin-3-one-4-ylmethyl)morpholine hydrogen maleate m.p. 175°–177° C.

The 4-benzyl-2-(4H-2,3-dihydro-1,4-benzoxazin-3-one-4-ylmethyl)morpholine hydroen oxalate used as starting material may be prepared as follows:

A mixture of 4-benzyl-2-toluene-p-sulphonyloxymethylmorpholine (12.4 g.) and the sodium salt prepared from 4H-2,3-dihydro-1,4-benzoxazin-3-one (5.1 g.) and sodium hydride (0.825 g.) in dimethylformamide (150 ml.) was heated under reflux under an atmosphere of nitrogen for 18 hours at 100° C. The dimethylformamide was evaporated in vacuo and the residue was partitioned between ethyl acetate (200 ml.) and water (200 ml.). The organic layer yielded an oil which was converted to a crystalline oxalate salt by standard procedures, then crystallised from ethanol to give 4-benzyl-2-(4H-2,3-dihydro-1,4-benzoxazin-3-one-4-ylmethyl)morpholine hydrogen oxalate, m.p. 165°–168° C.

EXAMPLE 2

The process described in Example 1 was repeated except that an equivalent amount of 4-benzyl-2-(2-oxo-1,2,3,4-tetrahydroquinol-1-ylmethyl)morpholine hydrogen oxalate was used as starting material in place of 4-benzyl-2-(4H-2,3-dihydro-1,4-benzoxazin-3-one-4-ylmethyl)morpholine hydrogen oxalate, and there was thus obtained 2-(2-oxo-1,2,3,4-tetrahydroquinol-1-ylmethyl)morpholine hydrogen oxalate, m.p. 170°–175° C. on trituration with ethyl acetate.

The 4-benzyl-2-(2-oxo-1,2,3,4-tetrahydroquinol-1-ylmethyl)morpholine hydrogen oxalate used as starting material may be prepared by repeating the second part of Example 1 using an equivalent amount of 1,2,3,4-tetrahydro-2-oxo-quinoline as starting material in place of 4H-2,3-dihydro-1,4-benzoxazin-3-one.

EXAMPLE 3

The process described in Example 1 was repeated except that an equivalent amount of 4-benzyl-2-(4H-2,3-dihydro-2,2-dimethyl-1,3-benzoxazin-3-one-4-ylmethyl)morpholine hydrogen oxalate was used as starting material in place of 4-benzyl-2-(4H-2,3-dihydro-1,4-benzoxazin-3-one-4-ylmethyl)morpholine hydrogen oxalate, and there was thus obtained 2-(4H-2,3-dihydro-2,2-dimethyl-1,4-benzoxazin-3-one-4-ylmethyl)morpholine hydrogen oxalate, m.p. 187°–190° C. on recrystallisation from methanol.

The 4-benzyl-2-(4H-2,3-dihydro-2,2-dimethyl-1,4-benzoxazin-3-one-4-ylmethyl)morpholine hydrogen oxalate used as starting material may be prepared by repeating the second part of Example 1 using an equivalent amount of 4H-2,3-dihydro-2,2-dimethyl-1,4-benzoxazin-3-one as starting material in place of 4H-2,3-dihydro-1,4-benzoxazin-3-one. There was thus obtained 4-benzyl-2-(4H-2,3-dihydro-2,2-dimethyl-1,4-benzoxazin-3-one-4-ylmethyl)morpholine hydrogen oxalate, m.p. 165°–175° C. on recrystallisation from ethanol.

EXAMPLE 4

The process described in Example 1 was repeated except that the (2S)-isomer of 4-benzyl-2-(4H-2,3-dihydro-1,4-benzoxazin-3-one-4-ylmethyl)morpholine hydrogen oxalate was used in place of the corresponding racemic compound as starting material. The maleate salt of the product was obtained by standard procedures and then crystallised from ethanol to give (2S)-2-(4H-2,3-dihydro-1,4-benzoxazin-3-one-4-ylmethyl)-morpholine hydrogen maleate, m.p. 150°–152° C., $[\alpha]_D^{25} - 5.8°$(c, 1 in methanol).

Similarly, using the (2R)-isomer of 4-benzyl-2-(4H-2,3-dihydro-1,4-benzoxazin-3-one-4-ylmethyl)morpholine there was obtained (2R)-2-(4H-2,3-dihydro-1,4-benzoxazin-3-one-4-ylmethyl)morpholine hydrogen maleate, m.p. 150°–151° C., $[\alpha]_D^{25} + 6.0°$(c, 1 in methanol).

The (2S)- and (2R)-isomers of 4-benzyl-2-(4H-2,3-dihydro-1,4-benzoxazin-3-one-4-ylmethyl)morpholine may be obtained by reacting the (2S)- and (2R)-isomers respectively of 4-benzyl-2-toluene-p-sulphonyloxymethylmorpholine with 4H-2,3-dihydro-1,4-benzoxazin-3-one in a similar manner to that described in the second part of Example 1. The products were obtained as gummy oxalates which were used without further purification.

The (2S)- and (2R)-isomers of 4-benzyl-2-toluene-p-sulphonyloxymethylmorpholine may be obtained as follows:

To a solution of 4-benzyl-2-(toluene-p-sulphonyloxymethyl)morpholine (18.1 g.) in methanol (100 ml.) was added a solution of (+)-toluene-p-sulphonylglutamic acid (16.0 g.) in methanol (50 ml.) and the mixture was allowed to crystallise during 12 hours. The mixture was filtered, the filtrate was put on one side, and the filtered solids (18.3 g.) were recrystallised from methanol (150 ml.) to obtain the (+)-toluene-p-sulphonylglutamic acid salt of (2S)-4-benzyl-2-(toluenep-sulphonyloxymethyl)morpholine (14.0 g.), m.p. 184° C. This salt was stirred with a mixture of 2N sodium hydroxide and ether. The ether layer was separated, dried and the ether was distilled to leave optically pure (2S)-4-benzyl-2-(toluene-p-sulphonyloxymethyl)morpholine as an oil, from which was prepared the hydrochloride m.p. 150° C., $[\alpha]_D^{25}$ + 19.4° (c, 5 in methanol).

The filtrate which had been put on one side was concentrated by evaporation in vacuo and the residual (2R)-4-benzyl-2-(toluene-p-sulphonyloxymethyl)morpholine was thus obtained as the (+)-toluene-p-sulphonylglutamic acid salt. This salt was stirred with a mixture of 2N sodium hydroxide and ether and the ether layer was separated, dried and evaporated to give the corresponding base. The hydrochloride of this base was obtained by standard procedures and was crystallised from acetone to give (2R)-4-benzyl-2-(toluene-p-sulphonyloxy-methyl)morpholine hydrochloride, m.p. 150° C., $[\alpha]_D^{25}$ − 19.4° (c, 5 in methanol).

EXAMPLE 5

Concentrated hydrobromic acid (20 ml.) was added to a solution of 2-(8-chloro-4H-2,3-dihydro-1,4-benzoxazin-3-one-4-ylmethyl)-4-phenoxycarbonylmorpholine (5.27 g.) in acetic acid (20 ml.) and the mixture was heated under reflux for 3 hours. The reaction mixture was diluted with water (40 ml.), a 50% w/v aqueous solution of sodium hydroxide was added to bring the pH to 11 and the mixture was then extracted with ethyl acetate. The extract afforded an oil which was converted to a maleate salt by standard procedures. The salt was crystallised to give 2-(8-chloro-4H-2,3-dihydro-1,4-benzoxazin-3-one-4-ylmethyl)morpholine hydrogen maleate, m.p. 152°–155° C.

The 2-(8-chloro-4H-2,3-dihydro-1,4-benzoxazin-3-one-4-ylmethyl)-4-phenoxycarbonylmorpholine used as starting material may be prepared as follows:

A solution of 6-chloro-2-nitrophenol (1.7 g.) and ethyl chloroacetate (2.1 ml.) in dimethylformamide (12 ml.) with potassium carbonate (1.5 g.) was stirred at 75°–80° C. for 3 hours. The mixture as poured into water (120 ml.) and extracted with ethyl acetate (4 × 50 ml.). The organic layer on evaporation yielded 6-chloro-2-nitrophenoxyacetic acid ethyl ester as a yellow oil.

A solution of 6-chloro-2-nitrophenoxyacetic acid ethyl ester (14.6 g.) in glacial acetic acid (120 ml.) and water (80 ml.) was treated with iron powder (7.0 g.) portion-wise and the mixture was heated under reflux with stirring for 1.5 hours. Filtration of the mixture and evaporation of the solvents in vacuo afforded a residue which was partitioned between ethyl acetate (200 ml.) and water (200 ml.). The organic layer on evaporation yielded a solid which crystallised from toluene to give 8-chloro-4H-2,3-dihydro-1,4-benzoxazin-3-one, m.p. 223°–226° C. (sealed tube)

The process described in the second part of Example 1 was repeated using an equivalent amount of 8-chloro-4H-2,3-dihydro-1,4-benzoxazin-3-one as starting material in place of 4H-2,3-dihydro-1,4-benzoxazin-3-one and there was thus obtained 4-benzyl-2-(8-chloro-4H-2,3-dihydro-1,4-benzoxazin-3-one-4-ylmethyl)morpholine hydrogen oxalate, m.p. 170°–173° C. after recrystallisation from ethanol. 4-Benzyl-2-(8-chloro-4H-2,3-dihydro-1,4-benzoxazin-3-one-4-ylmethyl)morpholine (5.83 g.) was dissolved in methylene chloride (100 ml.) and the solution was heated under reflux with phenylchloroformate (2.19 ml.) for 5 hours. The solvent was evaporated in vacuo and the residual oil was triturated with dry ether (100 ml.). There was thus obtained 2-(8-chloro-4H-2,3-dihydro-1,4-benzoxazin-3-one-4-ylmethyl)-4-phenoxycarbonylmorpholine, m.p. 134°–135° C.

EXAMPLE 6

Powdered zinc (1.0 g.) was added to a solution of 2-(4H-2,3-dihydro-1,4-benzthiazin-3-one-4-ylmethyl)-4-(2,2,2-trichloroethoxycarbonyl)morpholine (4.6 g.) in a mixture of methanol (100 ml.) and acetic acid (1 ml.) and the mixture was heated under reflux for 1.5 hours. The reaction mixture was filtered and the residual solid was extracted with boiling methanol. The extract and filtrate were combined and the solvents evaporated in vacuo. The residual oil was converted into a maleate salt by standard procedures. The salt was crystallised from ethanol to give 2-(4H-2,3-dihydro-1,4-benzthiazin-3-one-4-ylmethyl)morpholine hydrogen maleate, m.p. 168°–172° C.

The 2-(4H-2,3-dihydro-1,4-benzthiazin-3-one-4-ylmethyl)-4-(2,2,2-trichloroethoxycarbonyl)morpholine used as starting material may be prepared as follows:

The process described in the second part of Example 1 was repeated using an equivalent amount of 4H-2,3-dihydro-1,4-benzthiazin-3-one as starting material in place of 4H-2,3-dihydro-1,4-benzoxazin-3-one, and there was thus obtained 4-benzyl-2-(4H-2,3-dihydro-1,4-benzthiazin-3-one-4-ylmethyl)-morpholine hydrogen oxalate, m.p. 148°–153° C. on recrystallisation from ethanol.

A mixture of 4-benzyl-2-(4H-2,3-dihydro-1,4-benzthiazin-3-one-4-ylmethyl)morpholine (3.6 g.), 2,2,2-trichloroethyl chloroformate (1.54 ml.) and methylene chloride (100 ml.) was heated under reflux for 1 hour and the methylene chloride was then removed by evaporation in vacuo. The residual oil was dissolved in ethyl acetate and the solution was washed with 1N hydrochloric acid, then with 1N aqueous sodium carbonate and finally with water. The solution was dried, the solvent evaporated and the residual oil chromatographed on silica gel (60 g.) in chloroform (400 ml.). The column was eluted with ether to give 2-(4H-2,3-dihydro-1,4-benzthiazin-3-one-4-ylmethyl)-4-(2,2,2-trichloroethyoxycarbonyl)morpholine as a pale yellow oil, characterised by infra-red absorption at 1715 and 1670 cm$^{-1}$.

EXAMPLE 7

The process described in Example 1 was repeated using an equivalent amount of the appropriately substituted 4-benzyl-morpholine as starting material in place of 4-benzyl-2-(4H-2,3-dihydro-1,4-benzoxazin-3-one-4-ylmethyl)morpholine hydrogen oxalate and the following compounds were thus obtained:

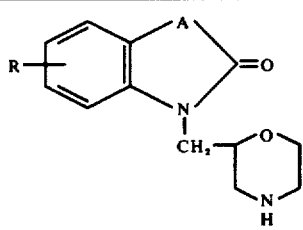

| A | R | Salt | m.p. (° C.) | Recrystallisation solvent |
|---|---|---|---|---|
| —O—CH$_2$— | 5-CH$_3$ | hydrogen maleate | 105–109 | methanol |
| —O—CH$_2$— | 6-CH$_3$O | hydrogen maleate | 155–158 | ethanol |
| —O—CH$_2$— | 6-n-C$_3$H$_7$O | hydrogen maleate | 107–113 | ethanol |
| —O—CH$_2$— | 7-CH$_3$ | hydrogen maleate | 172–175 | ethanol |
| —CH(CH$_3$)CH$_2$— | H | hydrogen maleate | 158–161* | ethanol |
| —CH$_2$— | H | hydrogen maleate | 161–163 | methanol |
| —O— | H | hydrogen oxalate | 245 (decomp.) | aqueous methanol |

* 1:1 mixture of diastereoisomers

The substituted 4-benzylmorpholines used as starting materials may be prepared by repeating the process described in the second part of Example 1 using an equivalent amount of the appropriate cyclic amide as starting material in place of 4H-2,3-dihydro-1,4-benzoxazin-3-one. The following compounds were thus prepared:

| A | R | Salt | m.p. (° C.) | Recrystallisation solvent |
|---|---|---|---|---|
| —O—CH$_2$— | 5-CH$_3$ | hydrogen oxalate | (oil) | — |
| —O—CH$_2$— | 6-CH$_3$O | hydrogen oxalate | 141–145 | acetone |
| —O—CH$_2$— | 6-n-C$_3$H$_7$O | hydrogen oxalate | 159–163 | ethanol |
| —O—CH$_2$— | 7-CH$_3$ | hydrogen oxalate | 176–179 | ethanol |
| —CH(CH$_3$)CH$_2$— | H | hydrogen oxalate | 63–70 | — |
| —CH$_2$— | H | hydrogen oxalate | 125–132 | ethanol |
| —O— | H | hydrogen oxalate | (oil) | — |

The 4H-2,3-dihydro-6-n-propoxy-1,4-benzoxazin-3-one used as starting material may be obtained by repeating the process described in Neth. Appl. 6, 511, 624 (Chemical Abstracts 1966, 65, 656) for the preparation of the corresponding 6-methoxy derivative. There was thus obtained 4H-2,3-dihydro-6-n-propoxy-1,4-benzoxazin-3-one, m.p. 101.5°–103.5° C. on recrystallisation from cyclohexane.

EXAMPLE 8

Sodium hydride (80% w/w dispersion in oil; 0.33 g.) was added to a solution of the toluene-p-sulphonic acid salt of 2-(2-hydroxyanilinomethyl)morpholine (1.9 g.) in dimethyl-formamide (50 ml.) in an atmosphere of nitrogen. The solution was stirred for 1 hour at 18° C., ethyl chloroacetate (0.64 ml.) was added and the mixture stirred for 1 hour at 18° C. The dimethylformamide was removed from the reaction product by evaporation in vacuo and the residue was partitioned between ethyl acetate and a saturated aqueous solution of sodium carbonate. The organic phase was separated, dried over magnesium sulphate and evaporated in vacuo. The residual oil thus obtained was converted to an oxalate salt by standard procedures and there was thus obtained 2-(4H-2,3-dihydro-1,4-benzoxazin-3-one-4-ylmethyl)morpholine hydrogen oxalate, m.p. 205°–208° C. on recrystallisation from methanol. The toluene-p-sulphonic acid salt of 2-(2-hydroxyanilinomethyl)morpholine may be prepared as follows:

A mixture of o-aminophenol (15 g.) and 4-benzyl-2-(toluene-p-sulphonyloxymethyl)morpholine (30 g.) was heated at 200° C. for 1 hour in an atmosphere of nitrogen. The reaction product was crystallised from ethanol to give 4-benzyl-2-(2-hydroxyanilinomethyl)morpholine as the toluene-p-sulphonic acid salt, m.p. 188°–190° C., which was hydrogenated in ethanol at atmospheric pressure using a 10% palladium-on-carbon catalyst. There was thus obtained 2-(2-hydroxyanilinomethyl)morpholine as the toluene-p-sulphonic acid salt, m.p. 176°–178° C. on recrystallisation from ethanol.

EXAMPLE 9

The toluene-p-sulphonic acid salt of 2-(2-hydroxyanilinomethyl)morpholine (0.19 g.) was dissolved in a mixture of acetone (5 ml.) and water (5 ml.). The solution was stirred at ambient temperature and chloroacetyl chloride (0.04 ml.) and 2N sodium hydroxide solution were added dropwise alternately so that the pH of the reaction solution remained between 3 and 4. The mixture was stirred for 1 hours. The pH of the solution was adjusted to 10 by addition of 2N sodium hydroxide solution and the mixture was stirred for 5 minutes. The solution was diluted with water (20 ml.) and extracted with chloroform (3 × 30 ml.). The chloroform extracts were dried and the chloroform removed by evaporation under reduced pressure. There was thus obtained 2-(4H-2,3-dihydro-1,4-benzoxazin-3-one-4-ylmethyl)morpholine, which may be converted to its hydrogen oxalate, m.p. 205°–208° C. on recrystallisation from methanol/ether.

EXAMPLE 10

A solution of 2-(4H-2,3-dihydro-2-ethoxycarbonyl-1,4-benzoxazin-3-one-4-ylmethyl)morpholine hydrogen oxalate (0.8 g.) in hydrochloric acid (2N., 30 ml.) was heated under reflux for 4 hours. The cooled solution was made alkaline and extracted with chloroform. The extract was washed with water, dried and the chloroform removed by evaporation in vacuo. There was thus obtained 2-(4H-2,3-dihydro-1,4-benzoxazin-3-one-4-ylmethyl)-morpholine which afforded the hydrogen maleate, m.p. 175°–177° C. on recrystallisation from methanol, by standard procedures.

The 2-(4H-2,3-dihydro-2-ethoxycarbonyl-1,4-benzoxazin-3-one-4-ylmethyl)morpholine used as starting material may be prepared as follows:

The toluene-p-sulphonic acid salt of 2-(2-hydroxyanilinomethyl)morpholine (1.9 g.) was dissolved in dimethylformamide (50 ml.). Sodium hydride (80% w/w dispersion in oil, 0.3 g.) was added to the solution and the mixture was stirred for 1 hour at 18° C. in an atmsophere of nitrogen, cooled to 5° C. and diethyl chloromalonate (0.89 ml.) added. The mixture was stirred at 10° C. for 1 hour and then at 18° C. for 48 hours, and was then poured onto a mixture of ice and ethyl acetate. The organic phase was separated and the ethyl acetate removed by evaporation in vacuo. The residual oil was chromatographed on magnesium silicate in a 1:1 v/v mixture of ethanol and ethyl acetate and there was thus obtained 2-(4H-2,3-dihydro-2-ethoxycarbonyl-1,4-benzoxazin-3-one-4-yl-methyl)-morpholine as an oil which was used without further purification.

EXAMPLE 11

A mixture of 4-[2-hydroxy-3-(2-hydroxyethylamino)-propyl]-4H-2,3-dihydro-1,4-benzoxazin-3-one (26.6 g.) and toluene-p-sulphonic acid (41.6 g.) in xylene (100 ml.) was heated under reflux for 3 hours, the water formed being collected in a Dean and Stark apparatus. The mixture was cooled to 60° C. and water (50 ml.) followed by 19N sodium hydroxide (18 ml.) was added. The aqueous layer was separated and extracted twice with ethyl acetate (100, 50 ml.). The combined ethyl acetate and xylene extracts were evaporated to dryness and the residue converted to a maleate salt by standard procedures to give 2-(4H-2,3-dihydro-1,4-benzoxazin-3-one-4-ylmethyl)morpholine hydrogen maleate, m.p. 175°–176° C. on recrystallisation from ethanol.

The above cyclisation was also effected by refluxing the starting material in 48% w/v hydrobromic acid. The 4-[2-hdroxy-3-(2-hydroxyethylamino)propyl]-4H-2,3-dihydro-1,4-benzoxazin-3-one used as starting material may be obtained as follows:

To a suspension of 4H-2,3-dihydro-1,4-benzoxazin-3-one (149 g.) in epichlorhydrin (400 ml.) was added distilled water (100 ml.). The mixture was stirred and heated to 50° C. and 4.2N aqueous sodium hydroxide (250 ml.) was added dropwise over 1 hour. The reaction mixture was stirred at 50° C. for a further 30 minutes, then cooled to 20° C. and allowed to separate. The lower organic layer was run off and washed with water (250 ml.). The excess epichlorhydrin was removed by evaporation under 14 m.m. pressure (maximum temperature 70° C.). Water (200 ml.) was then added to the reaction mixture and then removed by evaporation under 14 m.m. pressure (maximum temperature 70° C.). The crude epoxide was thus obtained as a clear viscous oil which was used without further purification. To the vigorously stirred crude epoxide (200.3 g.) at 20° C. was added rapidly a mixture of ethanolamine (480 ml.) and water (120 ml.) having a temperature of 24° C. After 17 minutes the reaction mixture reached a steady temperature of 57° C. Stirring was continued for a further 13 minutes, allowing the reaction mixture to cool to b 45° C. The excess water and ethanolamine were distilled off under 14 m.m. pressure at a maximum temperature of 100° C. Xylene (250 ml.) was added to the reaction mixture and any residual ethanolamine was removed by distilling off the xylene/ethanolamine azeotrope. The residue was cooled and recrystallised from methyl isobutyl ketone to give 4-[2-hydroxy-3-(2-hydroxyethylamino)propyl]-4H-2,3-dihydro-1,4-benzoxazin-3-one, m.p. 109.5°–110° C.

What I claim is:

1. A morpholine derivative of the formula:

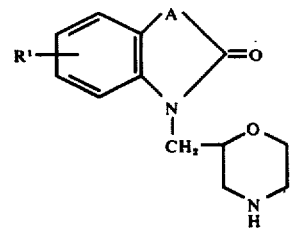

wherein $R^1$ is hydrogen or halogen, or alkyl or alkoxy of 1 to 3 carbons; A is a radical of the formula:

wherein $R^2$ and $R^3$, which may be the same or different, are hydrogen or alkyl of 1 to 3 carbons and B is sulphur, and the non-toxic, pharmaceutically-acceptable acid-addition salts thereof.

2. A morpholine derivative as claimed in claim 1 wherein $R^2$ and $R^3$ are hydrogen.

3. A morpholine derivative as claimed in claim 1 which is 2-(4H-2,3-dihydro-1,4-benzthiazin-3-one-4-ylmethyl)morpholine.

* * * * *